(12) United States Patent
Zawaideh et al.

(10) Patent No.: US 8,319,966 B2
(45) Date of Patent: **\*Nov. 27, 2012**

(54) OPTICAL METROLOGY SYSTEMS AND METHODS

(76) Inventors: Emad Zawaideh, Carlsbad, CA (US); Javier Ruiz, Oceanside, CA (US)

( * ) Notice: Subject to any disclaimer, the term of this patent is extended or adjusted under 35 U.S.C. 154(b) by 196 days.

This patent is subject to a terminal disclaimer.

(21) Appl. No.: 12/403,119

(22) Filed: Mar. 12, 2009

(65) Prior Publication Data
US 2009/0174883 A1   Jul. 9, 2009

Related U.S. Application Data

(63) Continuation-in-part of application No. 10/873,735, filed on Jun. 22, 2004, now Pat. No. 7,505,133.

(51) Int. Cl.
*G01J 4/00* (2006.01)

(52) U.S. Cl. ........................ 356/364; 356/368

(58) Field of Classification Search .......... 356/326–327, 356/600–640, 364–369; 250/225
See application file for complete search history.

(56) References Cited

U.S. PATENT DOCUMENTS

| | | | |
|---|---|---|---|
| 6,898,537 B1 * | 5/2005 | McGahan | 702/76 |
| 2003/0016358 A1 * | 1/2003 | Nagashima et al. | 356/364 |
| 2004/0141177 A1 * | 7/2004 | Zhao et al. | 356/369 |

* cited by examiner

*Primary Examiner* — Tri T Ton
(74) *Attorney, Agent, or Firm* — John R. Ross; John R. Ross, III

(57) ABSTRACT

Metrology systems and methods that measure thin film thickness and or index of refraction of semiconductor wafers with at least one deposited or grown thin film layer. The present invention measures near normal incidence and grazing angle of incidence reflection (using reflected broadband UV, visible, and near infrared electromagnetic radiation) from a small region on a sample. Embodiments of the system selectively comprise a near-normal incidence spectrometer/ellipsometer, a high angle of incidence spectrometer/ellipsometer, or a combination of the two.

16 Claims, 13 Drawing Sheets

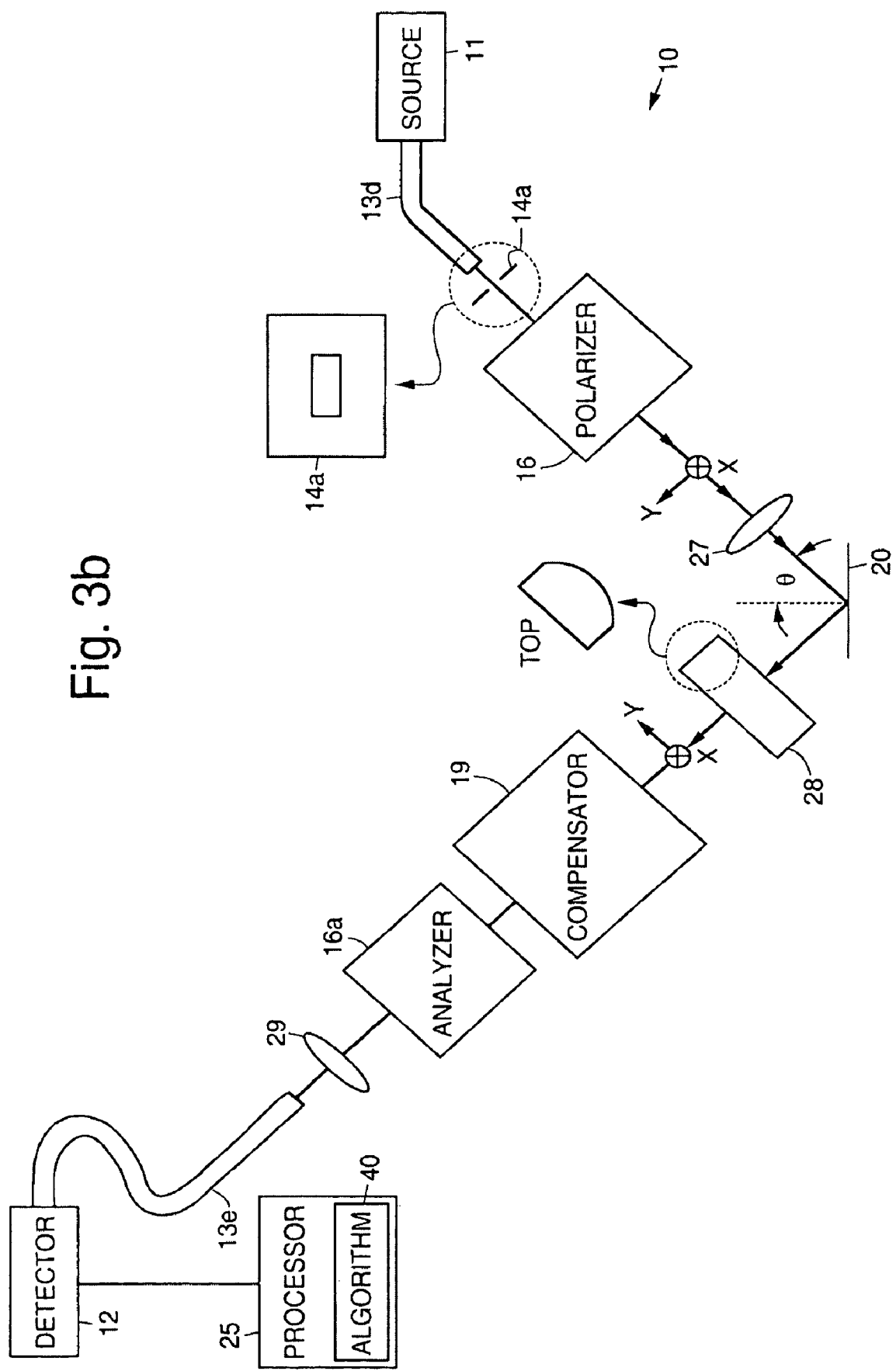

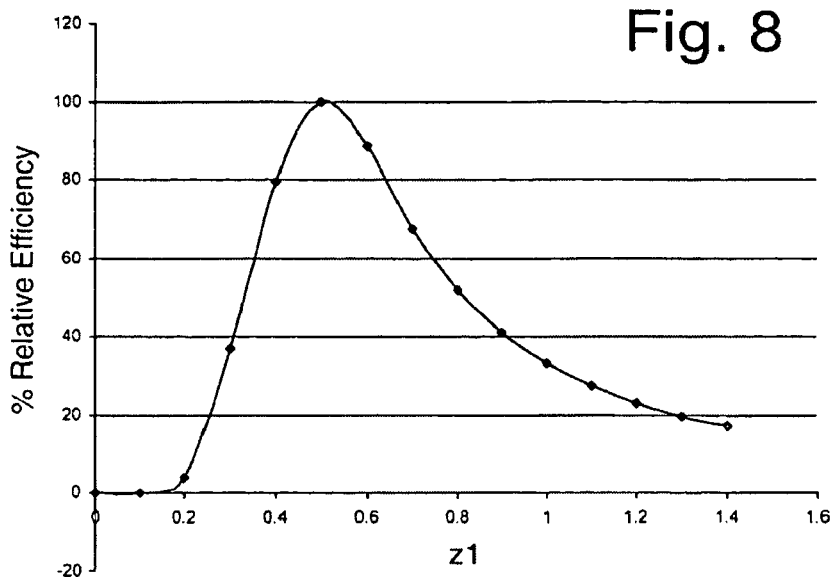
Fig. 8
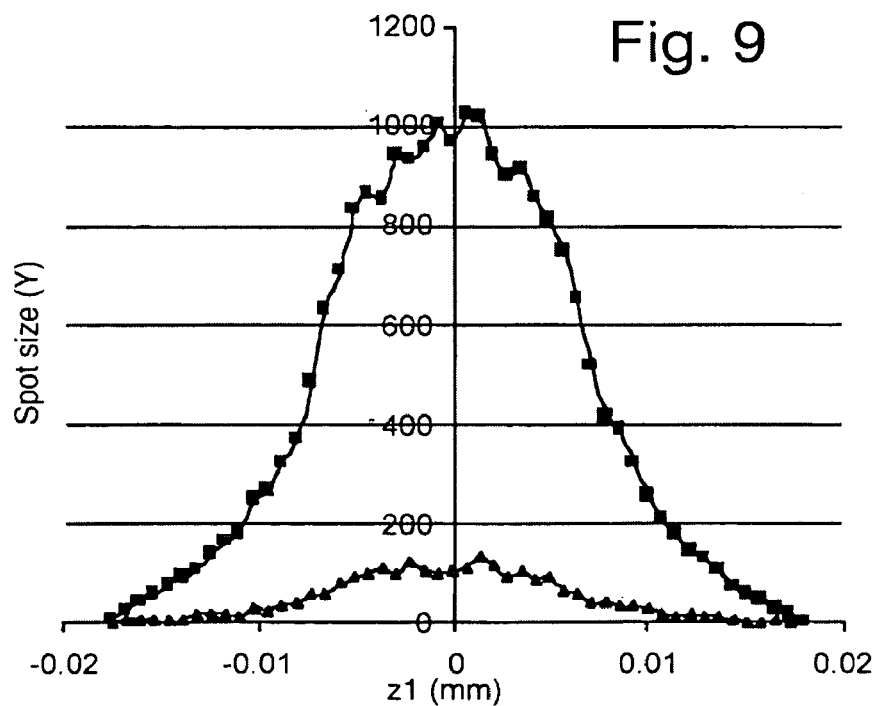
Fig. 9
Fig. 10
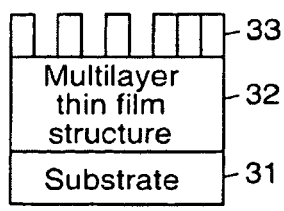
Fig. 11
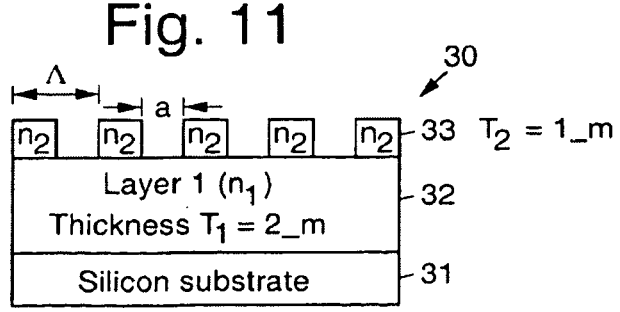

OPTICAL METROLOGY SYSTEMS AND METHODS

The present invention relates generally to the field of optical metrology, and more particularly, to broadband metrology for performing measurements of patterned thin films on semiconductor microelectronic wafers. This application is a continuation-in-part of application Ser. No. 10/873,735 filed Jun. 22, 2004 now U.S. Pat. No. 7,505,133; which is incorporated herein by reference.

BACKGROUND

For applications such as measurement of thin film thickness or index of refraction of semiconductor wafers with at least one deposited or grown thin film layer, it is desirable to measure near normal incidence reflection (using reflected broadband UV, visible and near infrared electromagnetic radiation) from a small region on the sample. Several methods currently exist for measuring small spot size near normal incidence spectroscopic reflection. However, there are drawbacks to each of these methods that are overcome by the present invention.

One method is to use a refractive microscope objective to focus electromagnetic radiation from a lamp onto a small region on a sample. The same microscope objective collects reflected electromagnetic radiation from the sample which is then directed by suitable beamsplitters and or other optics to a detector. The main drawback to this method is that the practical usable wavelength range is primarily limited to visible and near infrared regions of the electromagnetic radiation spectrum due to the extreme difficult) of designing a refractive objective that simultaneously spans the UV, visible, and near infrared portions of the electromagnetic spectrum.

This difficulty is primarily due to two reasons: a) the extreme difficulty of designing a color corrected objective due to the limited availability of materials that a lens designer has at his/her disposal that transmits in the UV portion of the spectrum and do not exhibit birefringence; and b) the extreme difficulty of designing and producing antireflection coatings for the lens elements of the objective that simultaneously covers the UV, visible, and near infrared portions of the electromagnetic radiation spectrum. U.S. Pat. No. 6,587,282 addresses designing a broadband refractive objective for use between 185 and 900 nm by using a three-element objective. However, this patent does not address the difficulty in designing and producing antireflection coatings that covers the 185-900 nm wavelength range.

Another method is to use an all-reflective type objective with spherical mirrors. Cassegrain, Gregorian, and Schwarzschild arrangements are examples of such objectives. These all-reflective objectives have several advantages over refractive objectives. They are completely achromatic and as such are only limited in wavelength range by the availability of reflective coatings that cover the desired region of the electromagnetic spectrum. Also, aberrations due to spherical mirrors are typically much less than those of equivalent refractive elements.

The major drawback to these types of objectives is that they all have central obscurations in the aperture. This central obscuration greatly reduces system efficiency. One can compensate by using an objective with a high numerical aperture (NA). However, this introduces complexities in the extraction algorithm for the thin film thickness and index of refraction since the measured reflectance must in general be modeled as a weighted integral of the reflectance summed over angle of incidence. This requires that one know the intensity versus angle distribution of the electromagnetic radiation which can be further complicated by the fact that this intensity/angle distribution may have wavelength dependency. Furthermore, by using a high NA, the polarization state of the incident electromagnetic radiation also becomes important and must be known and or controlled.

Another method is to use a catadioptric design that employs a combination of spherical mirrors and refracting elements. The purpose of the refracting elements is to correct the aberrations due to the spherical mirror(s). These arrangements are also difficult to design and produce antireflection coatings for, and also have the above mentioned problems related to central obscuration of the aperture.

Another method is to use all reflective off-axis objectives. These objectives do not possess a central obscuration in the aperture. They may be constructed with combinations of spherical and or aspherical mirrors. Typically, prior art designs employ three mirrors and are very sensitive to alignment.

Another method is to use multiple objectives on a rotating turret or linear actuator, each color corrected for a certain region of the electromagnetic spectrum. This is very time consuming since the each objective must be positioned and focused to the correct height in order to take a measurement. Also, insuring that each objective measure from the same region of the sample becomes quite complicated.

The present invention overcomes the above-discussed limitations of the prior art.

It is often desirable to measure polarized reflectance data at near-normal incidence. One example application where measurement of polarized data is useful is in the measurement of critical dimensions (line width, step height, and sidewall angles) of patterned semiconductor wafers. Critical dimension test patterns typically include sets of parallel lines produced on a wafer. The wafer with the patterned parallel lines is placed in the instrument.

The actual angle that the parallel lines make with respect to established axes of the instrument is, in general, not known. It is highly desirable that the measurement is independent of sample orientation, or in other words, the instrument is able to, as part of the measurement, detect or measure the actual rotational orientation of the fast-axis of the sample.

In the following discussion, the source path is the path the electromagnetic radiation takes in traveling from the source of the electromagnetic radiation up to and before reflection from the sample. Also, in the following discussion, the detector path is the path the electromagnetic radiation takes after reflecting from the sample and traveling to the detector.

By inserting a rotatable polarizer that is in both the source (forward) path and detector (return) path of the electromagnetic radiation incident upon and emergent from the sample, a normal incidence reflection ellipsometer is achieved. This type of ellipsometer, where a single polarizing element acts as both polarizer of the incident electromagnetic radiation and analyzer of the reflected electromagnetic radiation from the sample, is capable of measuring ellipsometric parameters psi and delta as well as the sample's orientation of the fast axis with respect to previously established axes of the instrument.

At some point in the path of the normal incidence ellipsometer, due to the facts that the detector and illumination source cannot physically occupy the same volume and that the source and detector paths are nearly coincident at the sample, the source illumination path must be separated from the detector path. This requirement has been handled in several different ways by the prior art.

In general, the prior art falls into three different categories, as discussed below.

(1) Separation of source and detector paths is accomplished via a polarizing beamsplitter. In this arrangement, electromagnetic radiation from a source is first transmitted or reflected by a polarizing beamsplitter. It then impinges on a sample, is reflected by the sample, is reflected or transmitted by the polarizing beamsplitter, and is then transmitted by a rotatable analyzer towards a detector. This arrangement has a significant drawback in that the sample must be rotated in order to determine the orientation of the fast axis of the sample. Also, this arrangement does not allow for measurement of the full possible range of the ellipsometric parameter, delta. Delta is limited to 0 to 180 degrees, instead of 0 to 360 degrees.

(2) Separation of source and detector paths is accomplished by designing a system with a non-zero angle of incidence (near normal angle of incidence) at the sample. In this arrangement, the detector and source paths are never coincident. Examples of this type of ellipsometer are described in Kamiya et al, Phys. Rev. B 46, 15894 (1992c) and Aspnes et al, J. Vac. Sci. Technol. A 6, 1327 (1988b). Due to the angle separation and displacement of the beams, these systems typically must have separate polarizer elements to perform the polarizing and analyzing functions. Having two polarizers instead of a single polarizing element is more expensive and adds complexity to the ellipsometer calibration and sample measurement.

(3) Separation of source and detector paths is accomplished via a non-polarizing beamsplitter. In this arrangement, electromagnetic radiation from the source is first transmitted or reflected by a non-polarizing beamsplitter; then transmitted by a rotatable polarizer, impinges on the sample, it is then reflected by the sample, is transmitted by the rotatable polarizer, and is reflected or transmitted by the non-polarizing beamsplitter towards a detector. These systems have the advantages of a single polarizing element, and that ellipsometric parameters, psi and delta, and the relative orientation of the fast axis of the sample with respect to previously established axes of the system, are directly measured.

One significant drawback to this system is that it is very difficult to design and produce a 45 degree (45 degrees is desirable for an easy to align compact system) broadband non-polarizing beamsplitter that effectively covers the UV, visible and near infrared regions of the electromagnetic spectrum. Also, calibrating the system (ellipsometer) to account for the necessary correction parameters due to such a non-polarizing beam-splitter adds significant complexity to the ellipsometer calibration. If the non-polarizing beamsplitter is perfect, no correction parameters are needed. A perfect non-polarizing beamsplitter reflects incident s and p polarized electromagnetic radiation equally, and transmits incident s and p polarized light equally as well.

If one arranges the system components so that the angle of incidence at the non-polarizing beamsplitter is very small, then the design of the non-polarizing beamsplitter becomes much more feasible. An example of such an arrangement is given in Cui et al, Applied Optics, Vol. 35, No. 13, 2235-2238, 1996. In this arrangement, the angle of incidence at the non-polarizing beamsplitter is less than 1 degree.

One significant drawback to this type of system arrangement is that the detector path after reflection from the non-polarizing beamsplitter travels back towards the sample almost coincident and in the same direction as the source path. In order to prevent the detector from blocking the electromagnetic radiation from the source reaching the sample, this requires that the distance between the non-polarizing beamsplitter and the sample be quite long; in other words, this type of arrangement does not lend itself to a compact system design.

Another problem associated with the general arrangement of a single polarizing element common to the source and detector paths), is that electromagnetic radiation reflected from the polarizer itself may reach the detector. This reflection can normally be subtracted from the measurement by performing a suitable background measurement. Nevertheless, it is highly undesirable since it effectively degrades the system signal to noise ratio and makes measurement of samples with very low reflection highly problematic.

Typically this reflection from the polarizer that reaches the detector is limited by applying antireflection coatings to both faces of the polarizing element. For broadband ellipsometers, this is problematic because as mentioned previously, it is extremely difficult to design and produce effective antireflection coatings that simultaneously cover the UV, visible, and near infrared portions of the electromagnetic radiation spectrum.

The present invention also overcomes these limitations of the prior art.

SUMMARY OF THE INVENTION

The present invention provides for metrology systems or instruments that overcome the limitations of the prior art discussed above. The present invention provides for measurement of thin film thickness or index of refraction of semiconductor wafers with at least one deposited or grown thin film layer. The present invention measures near normal incidence reflection and high angle of incidence (using reflected broadband UV, visible and near infrared electromagnetic radiation) from a small region on a sample.

Embodiments of the system selectively comprise a near-normal incidence reflectometer or ellipsometer, a high angle of incidence ellipsometer-reflectometer, or a combination of the two. A preferred system embodies both the near-normal incidence and high angle of incidence ellipsometer-reflectometers. More particularly, the preferred embodiment of the present invention combines an improved near-normal incidence reflectometer capable of measuring spectroscopic polarized reflectance and near normal incidence spectroscopic ellipsometric data from a small region on a sample with an improved high incidence angle spectroscopic ellipsometer that measures ellipsometric and or polarized reflectance data at a high angle of incidence.

In one embodiment of the present invention comprising the near-normal incidence ellipsometer-reflectometer, a single polarizing element is used. In this embodiment, separation of source and detector paths is achieved without the use of a non-polarizing beamsplitter, thus avoiding the previously discussed drawbacks. Also, the optical design of the present invention greatly minimizes the level of reflected electromagnetic radiation from the polarizer reaching the detector. This is accomplished without the use of broadband antireflection coatings.

More particularly, an exemplary embodiment of the near-normal incidence ellipsometer-reflectometer employs a fiber-optic cable and two paraboloid mirrors. The near-normal incidence ellipsometer-reflectometer comprises a ellipsometer when a polarizer is used, and a reflectometer when no polarizer is used (when only non-polarized reflectance data is needed). A cylindrical lens is preferably used to obtain high efficiency and short measurement time yet low range of angle of incidence at a sample.

An algorithm is employed with the near-normal incidence ellipsometer (i.e., system with polarizer) that allows for quick extraction of critical dimension (CD) measurement data. The algorithm or method extracts data indicative of the difference between ordinary and extraordinary indices of refraction of an anisotropic thin film deposited or grown on the sample. This algorithm combines the power spectral density of s and p polarized normal incidence reflectance data to uniquely generate the index of refraction difference between the s and p axes. When measuring patterned samples such as sets of parallel lines produced on a wafer, this information may then be used to extract line width, step height, and sidewall angles of the patterned lines (i.e., critical dimensions). In addition, the near normal-incidence data may be combined with spectroscopic or single wavelength ellipsometric data and/or polarized spectroscopic reflection data obtained at a non-normal high angle of incidence to extract film thickness and or index of refraction of the thin film layer(s) deposited or grown on the sample.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which:

FIG. 8 is a graph showing percent relative efficiency versus distance that the focus of the second paraboloid mirror is below the surface of the sample;

FIG. 9 is a graph showing number of rays versus spot size Y with and without the cylindrical lens;

FIG. 10 illustrates an typical sample having a substrate having a multilayer thin film structure disposed thereon;

FIG. 11 illustrates an exemplary sample having a substrate having a multilayer thin film structure disposed thereon;

DETAILED DESCRIPTION

Figure 1:
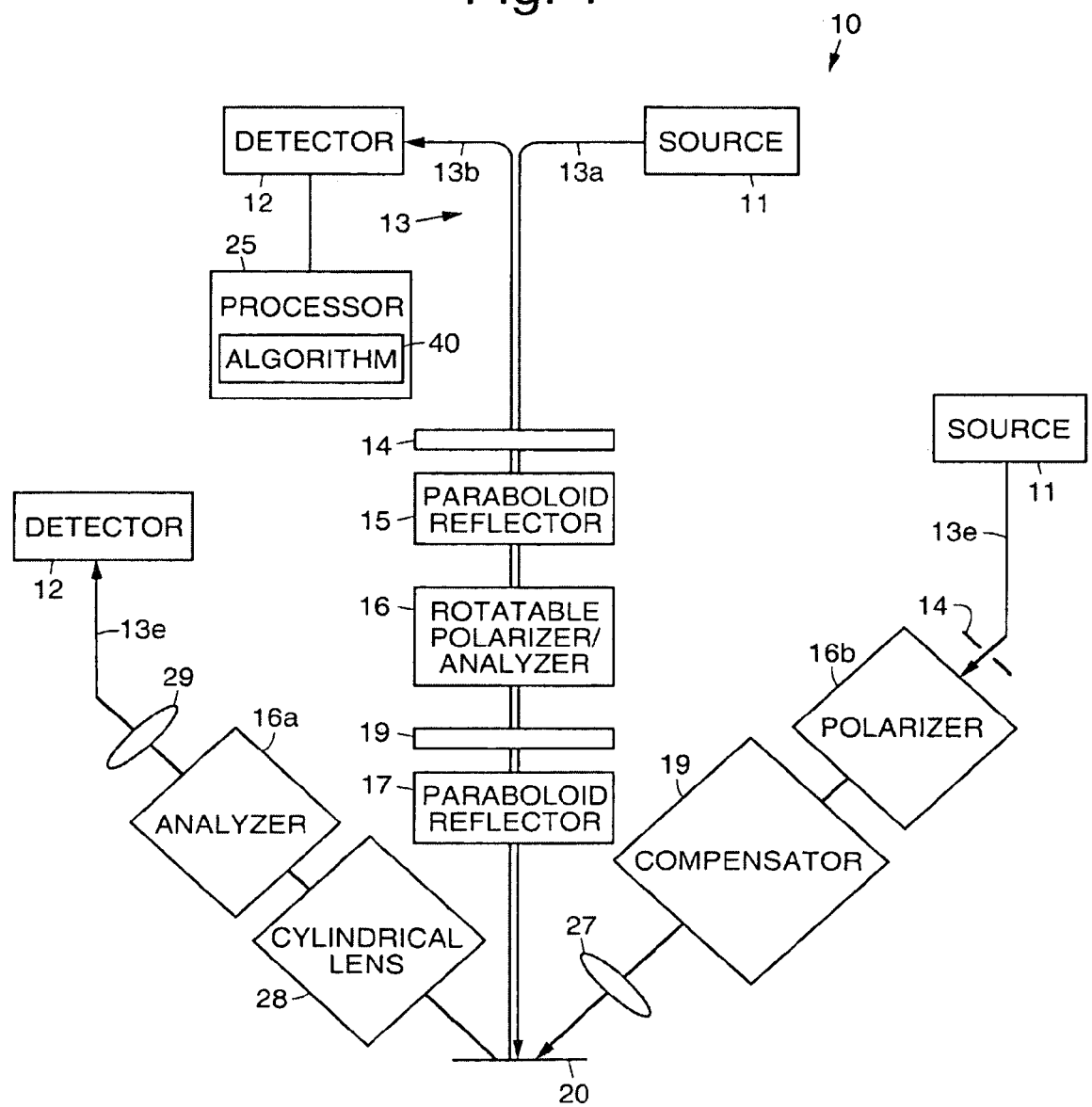
FIG. 1 illustrates an exemplary metrology system in accordance with the principles of the present invention.

Referring to the drawing figures, FIG. 1 illustrates an exemplary metrology system 10 or instrument 10 in accordance with the principles of the present invention. The metrology system 10 shown in FIG. 1 includes two subsystems, a near-normal metrology system 10 and a high angle of incidence metrology system 10. The present system 10 or instrument 10 may comprise either the near-normal metrology system 10, the high angle of incidence metrology system 10, or both. Also, when the near-normal incidence system 10 includes a polarizer 16, it forms an ellipsometer, and when no polarizer 16 is used, it forms a reflectometer. The components of the systems 10 designated by reference numeral in FIG. 1 are discussed in detail in FIGS. 2 and 3a-3c.

The systems 10 have the following measurement capabilities. They produce broadband small spot size polarized near-normal incidence reflectance data. They produce broadband small spot size ellipsometric data. They produce fast-axis orientation of a sample 20 (if the sample 20 is anisotropic). They produce broadband small spot-size polarized non-normal high angle of incidence data. They produce broadband small spot-size non-normal high angle of incidence ellipsometric data. The systems 10 measure patterned semiconductor wafers, by measuring regions smaller than 50 by 50 microns.

Figure 2:
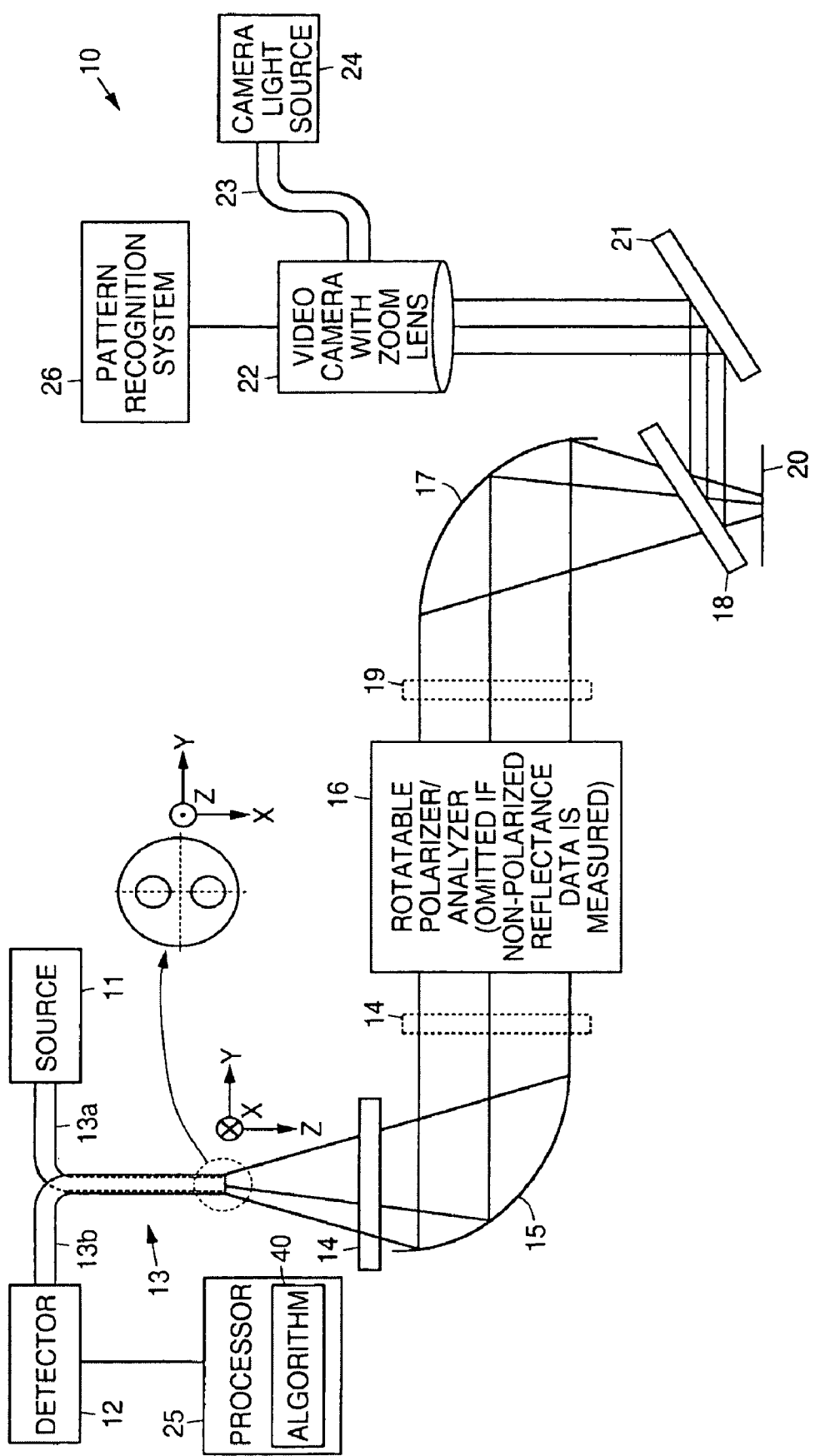
FIG. 2 illustrates an exemplary embodiment of a near-normal incidence metrology system in accordance with the principles of the present invention.

FIG. 2 illustrates an exemplary embodiment of a near-normal metrology system 10 in accordance with the principles of the present invention. The near-normal metrology system 10 or instrument 10 comprises an ellipsometer or a reflectometer, depending upon its configuration.

As is shown in FIG. 2, the near-normal metrology system 10 comprises a broadband light source subsystem 11 and a normal-incidence detector subsystem 12. A broadband light source subsystem 11, model OMT Is-xe75 light source, manufactured by OMT (Optische Messtechnik Gmbh), for example, may be used in the system 10. A detector subsystem 12, model S2000 spectrometer, manufactured by Ocean Optics, for example, may be used in the system 10.

A normal incidence focusing subsystem 15, 17 comprising first and second off-axis reflective paraboloid mirrors 15, 17 is used to focus light onto a sample 20 under measurement to be measured. The detector subsystem 12 is coupled to a processor 25 that is responsible for data collection, data reduction, display and interface to a user of the system 10. The processor 25 comprises an algorithm 40 that is used to quickly extract critical dimension (CD) measurement data relating to the sample 20.

A fiber-optic reflection probe 13 or cable assembly 13 or cable system 13 comprising a source fiber 13a and a detector fiber 13b, that respectively couple the near-normal incidence source subsystem 11 to the normal incidence focusing subsystem 15, 17, and couples the normal incidence focusing subsystem 15, 17 to the normal-incidence detector subsystem 12.

An optional adjustable aperture 14 may be used to control the normal incidence illumination cone angle. This adjustable aperture 14 may be placed before or after the first off-axis reflective paraboloid mirror 15 along the light path to the sample 20.

A rotatable polarizer/analyzer 16 is optionally disposed between the first and second off-axis reflective paraboloid mirrors 15, 17. The rotatable polarizer/analyzer 16 is employed in the system 10 to measure ellipsometric data. It is not used if only non-polarized reflectance data is collected.

An optional (rotatable or phase modulated) compensator 19 may also be disposed along the optical path between the first and second off-axis reflective paraboloid mirrors 15, 17. The rotatable or phase modulated compensator 19 is used to modulate the polarization state of the electromagnetic radiation that will impinge on the sample.

In addition, a beamsplitter 18 along with an optional mirror 21 may be used to couple light reflected from the sample 20 to a camera 22-24 and pattern recognition system 26 used to view the position of the measurement beam on the sample 20.

The camera 22-24 and pattern recognition system 26 comprises a video camera 22 having a zoom lens, and a camera light source 24 coupled to the camera 22 by way of a fiber optic cable 23.

All embodiments of the near-normal metrology system 10 employ two off-axis reflective paraboloid mirrors 15, 17 to demagnify the source subsystem 11 that provides the electromagnetic radiation. These off-axis paraboloidal reflectors 15, 17 are a circular segment from one side of a full paraboloid. The preferred type of reflector 15, 17 is a replicated metal mirror coated with aluminum and magnesium fluoride (MgF$_2$) overcoat. Commercial mirrors with surface irregularity of less than two wavelengths at 632 nm are commercially available and are suitable for employment in the present invention. Such reflectors are available from Spectra-Physics, Mountain View, Calif., for example.

Electromagnetic radiation from the source subsystem 11 is focused by optical elements within the source subsystem 11 onto the center of a fiber-optic output connector of the source subsystem 11. Both the source subsystem 11 and fiber-optic cable assembly 13 have mating SMA connectors. There are several ways to position the source fiber 13a of the fiber-optic cable assembly 13 at the output source of the source subsystem 11. SMA connectors are convenient since many commercial electromagnetic radiation sources suitable for optical metrology applications have SMA connectors on their output, and most manufacturers' of custom fiber-optic cable assemblies also provide SMA connectors that allow easy connection to such sources.

The fiber-optic cable assembly 13 incorporates two fibers 13a, 13b that are preferably made of fused silica which transmits UV electromagnetic radiation. The core diameter of each fiber 13a, 13b is preferably the same. The total diameter (core and cladding) of each fiber 13a, 13b is also preferably the same. The preferred core diameter is 200 microns and a preferred total diameter (core and cladding and buffer) is 265 microns. This is the diameter used in a reduced to practice embodiment of the system 10.

The core diameter choice is driven by several factors. Commercial fibers that are solarization resistant to UV electromagnetic radiation are difficult to procure if the fiber core diameter is less than 200 microns. Choosing a core diameter greater than 200 microns requires a larger demagnification factor in order to achieve a 40 by 40 micron measurement region on the sample 20. In order to maintain the same system collection efficiency, this requires larger diameter components and a longer path length (i.e., a larger instrument envelope and more expensive components) or a smaller working distance between the sample 20 and the second off-axis paraboloid mirror 17 and an incident cone angle on the sample 20.

The two off-axis paraboloidal reflectors 15, 17 that were selected for use in the reduced to practice embodiment of the system 10 were Spectra-Physics off-axis paraboloidal reflectors. Specifications for these reflectors 15, 17 may be found at page 109 of the 2004 Spectra-Physics components catalog, for example. A demagnification factor of 4 was chosen. This was achieved by employing an off-axis paraboloid reflector with effective focal length of 8 inches for the first off-axis paraboloid mirror 13a, and by employing an off-axis paraboloid reflector with effective focal length of 2 inches for the second off-axis paraboloidal mirror 17. The demagnification factor is given by the ratio of the effective focal lengths of the two off-axis paraboloidal mirrors 15, 17.

As will be explained below, the effective demagnification is larger than 4 due to further demagnification resulting from lateral displacement of detector fiber 13b and source fiber 13a from the focal point of the first off-axis paraboloid mirror 15.

In the preferred embodiment, the section of the full paraboloid is chosen such that the optical axis is bent by +/−90 degrees after reflection from the off-axis paraboloid.

The fiber-optic cable assembly 13 has three ends each terminated with SMA connectors. These ends are designated 'source', 'detector', and 'sample'. The source end has a single fiber at its center. This fiber is referred to as the 'source' fiber. The detector end similarly has a single fiber at its center. This fiber is referred to as the 'detector' fiber. Both the source fiber and detector fiber meet at the 'sample' end of the fiber assembly (see FIG. 2). These fibers are symmetrically centered about the center of the 'sample' end. Preferably the circumferences of the two fibers touch at the center of the sample end. The lateral distance between the centers of the detector and source fibers are labeled 'd'.

The center of the fiber sample end is preferably located at the focus of the first off-axis paraboloid mirror 15. The preferable orientation of the detector and source fibers 13a, 13b is such that if one draws a line segment between the centers of the fibers 13a, 13b, this segment should be orthogonal to a line segment drawn between the focus and vertex of the paraboloid.

The fiber-optic cable assembly 13 is connected to the electromagnetic radiation source 11 by means of the mating SMA connectors. The electromagnetic radiation that is focused onto the center of the source fiber output connector is coupled into the source fiber 13a of the fiber-optic cable assembly 13 and travels along the source fiber 13a until it reaches the end of the source fiber 13a at the sample end of the fiber-optic cable assembly 13. At this point, electromagnetic radiation emanates from the source fiber 13a in a diverging cone.

The electromagnetic radiation passes through an adjustable aperture plate 14. The aperture plate 14 limits the maximum angle of incidence at which the electromagnetic radiation may impinge on the sample 20. Preferably, the aperture plate 14 is motorized and is capable of total electromagnetic radiation extinction so that background noise may be measured. In an alternative embodiment (shown using dashed lines), the aperture plate 14 is located between the first and second off-axis paraboloid mirrors 15, 17.

In order to decrease measurement time, the maximum angle of incidence at the sample 20 may be increased to the maximum value that the system 10 allows without adversely affecting the thin film measurement if the total thickness of the thin films deposited or grown on the sample 20 is small. If however, the total thickness of the thin films deposited or grown on the sample 20 is large, the aperture plate 14 may be closed to only admit electromagnetic radiation that will impinge on the sample 20 with a very small range of angles. The reason for this is that the measured reflection at any given wavelength is the average reflection response integrated over angle of incidence, thickness variation within the measurement spot, and the actual wavelength range covered by the detector pixel. For thick films, the collection of large angles has the tendency to inhibit the reflection oscillations versus wavelength that are very instrumental in determining optical thickness of the film(s) on the sample.

The electromagnetic radiation next impinges on the first off-axis paraboloid reflector 15. Since the impinging cone of electromagnetic radiation emanating from the fiber 13a is in very close proximity to the focus of the paraboloid and since the fiber diameter dimension is small compared to paraboloid effective focal length, the reflected electromagnetic radiation from the first paraboloid reflector 15 is very nearly collimated.

The electromagnetic radiation then passes through the polarizer 16. Note that in an alternative embodiment of the system 10, in which the normal incidence subsystem does not collect ellipsometric data, but only non-polarized reflectance data, the polarizer 16 is omitted.

Some rays are reflected by the polarizer 16. In a preferred embodiment of the system 10, the polarizer 16 does not have antireflection coatings applied to its surfaces (i.e., it is an uncoated polarizer 16). It is difficult to apply antireflection coatings that simultaneously cover the UV, visible, and near infrared portions of the electromagnetic spectrum. It is easy to see that upon return that these rays primarily strike the source fiber 13a and not the detector fiber 13b, and thus are not collected by the system 10. Hence, one benefit of the present invention is that rays reflected by the polarizer 16 are for the most part not collected by the detector system 12. This is accomplished without the use of anti-reflection coatings.

To measure psi and delta and the orientation of the fast axis of a sample 20, the polarizer 16 rotates about the optical axis. Alternative embodiments of the system 10 employ a fixed polarizer 16 followed by a rotating compensator 19 or a fixed polarizer 16 and a phase modulated compensator 19. However, these embodiments do not allow for measurement of the orientation of the fast-axis of the sample 20.

In another alternative embodiment, the polarizer 16 is positioned between the sample fiber end of the fiber-optic cable assembly 13 and the first off-axis paraboloid mirror 15. The rays reflected by the polarizer 16 in this embodiment of the system 10 diverge after reflection from the polarizer 16 and have even less tendency of being collected by the system 10 than in the preferred embodiment of the system 10. Also, the required clear aperture of the polarizer 16 in this embodiment is smaller than the required aperture in the preferred embodiment. In the preferred embodiment, the polarizer 16 is placed in a location in the optical path where the electromagnetic radiation is collimated. In the above-mentioned embodiment, the polarizer 16 may be placed in close proximity to the sample end of the fiber-optic cable assembly 13. In this location, the clear aperture need only be as large as the base diameter of cone of electromagnetic radiation passing through the polarizer 16. However, one disadvantage of this embodiment is that the polarizer 16 is not as effective when the range of incident angles is large.

Next, the polarized electromagnetic radiation impinges on the second off-axis paraboloid mirror 17. The second off-axis paraboloid mirror 17 is positioned and orientated such that its focus is coincident with a desired measurement point on the sample 20 and also such that it may receive nearly collimated polarized electromagnetic radiation that has been transmitted by the polarizer 16.

The polarized electromagnetic radiation is next reflected from the second off-axis paraboloid mirror 17. Since the electromagnetic radiation incident upon the second off-axis paraboloid mirror 17 is nearly collimated and the second off-axis paraboloid mirror 17 is orientated and positioned so that focus of the second off-axis paraboloid mirror 17 is coincident with a point just below the desired measurement point on the sample 20, the reflected polarized electromagnetic radiation from the second off-axis paraboloid mirror 17 impinges in a converging cone onto the sample 20 in a small region centered about the desired measurement point.

Electromagnetic radiation impinges on a region larger than the actual measured region. However, as will be explained below, rays that do impinge on the sample 20 outside the desired measurement region ultimately miss the detector fiber 13b and are not collected.

For the purposes of further discussion the distance that the focus of the second off-axis paraboloid mirror 17 is above or below the surface of the sample is labeled as 'z1'. The following convention is chosen for the sign of z1; if the focus is below the surface of the sample 20, z1 is positive, and if above the surface, z1 is negative.

The polarized electromagnetic radiation is next reflected from the sample 20 in a diverging cone. In general, if the sample 20 has any anisotropy, the polarization state of the electromagnetic radiation is altered after reflection from the sample. Also, the amplitude of electromagnetic radiation is altered after reflection from the sample. It is the purpose of the instrument 10 to measure this change in amplitude as well as the change in the polarization state.

Next, the polarized electromagnetic radiation impinges on the second off-axis paraboloid mirror 17. Since the impinging cone of electromagnetic radiation emanating from the sample 20 is in very close proximity to the focus of the second off-axis paraboloid mirror 17, the reflected electromagnetic radiation from the second off-axis paraboloid mirror 17 is very nearly collimated.

The electromagnetic radiation then passes through the polarizer 17. Note again that in an alternative embodiment, in which the normal incidence subsystem 10 does not collect ellipsometric data, but only non-polarized reflectance data, the polarizer 17 is omitted.

Next, the polarized electromagnetic radiation impinges on the first off-axis paraboloid mirror 15. Since the first off-axis paraboloid mirror 15 is positioned and orientated such that its focus is coincident with the center of the sample end of the fiber-optic cable assembly 13, and incident electromagnetic radiation is nearly collimated, reflected light from the first off-axis paraboloid mirror 15, impinges on the sample end of the fiber-optic cable assembly 13 in a converging cone. The distance z1 is adjusted to a height to maximize the number of rays that strike the detector fiber.

Since the source and detector fibers 13a, 13b are not located at the focus of the first off-axis paraboloid mirror 15 (each is actually laterally displaced by d/2), maximum collection efficiency is only achieved when the focus of the second off-axis paraboloid mirror 17 is below the surface of the sample 20. In fact, when the second off-axis paraboloid mirror 17 is positioned so that its focus is coincident with the sample 20, the rays are returned primarily to the source fiber 13a, not the detector fiber 13b, and rays returning to the source fiber 13a are not collected by the detector system 12. So to achieve any type of efficiency the sample must be positioned slightly above the focus of the second off-axis paraboloid mirror 17

Figure 4:
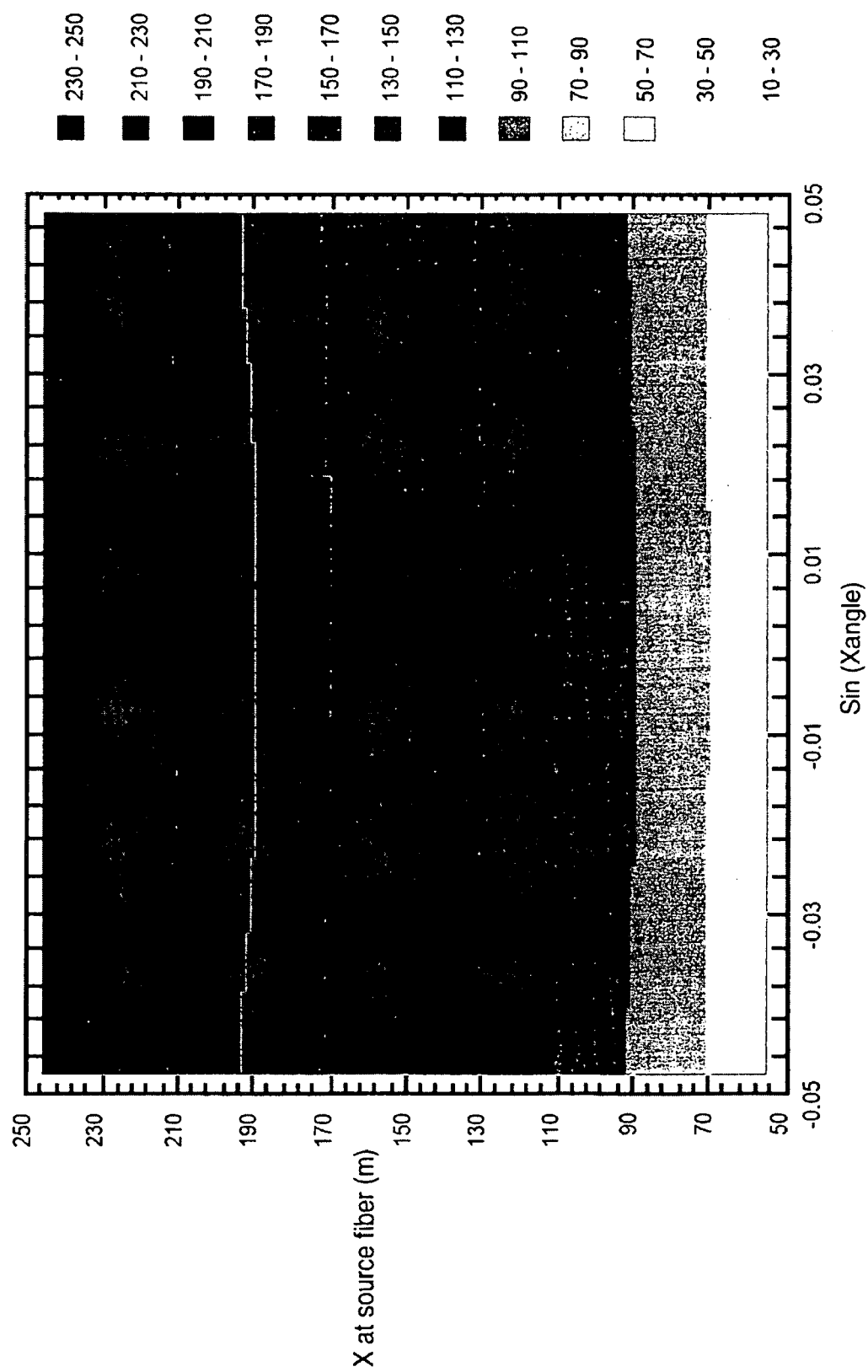
FIGS. 4-7 are simulation graphs relating to the present invention.

To illustrate this point, a simulation of final X position versus X position of a ray from source fiber and sine of the starting ray angle is shown in FIG. 4. For this simulation, the Y position was set to zero. The X position is varied from 0.050 mm to 0.250 mm. This corresponds to the center of the source fiber 13a placed on the positive X axis location (0.15, 0). The center of the detector fiber 13b is located at (−0.15, 0). In order for a ray to be collected by the system 10, the X return value should be within the core of the detector fiber 13b which spans −0.25 to −0.05 mm. For this simulation, we have chosen a value of d equal to 0.3 mm. At this value of d, the fibers are separated by 0.035 mm at their closest points. The sine of the starting angle at the source fiber was varied from −0.05 to 0.05. This corresponds to an angle range of −2.87 to 2.87 degrees at the source fiber 13a. With the value of z1 set equal to zero, the focus of the second off-axis paraboloid mirror 17 is exactly coincident with the sample 20. As can be seen from FIG. 4, all of the rays return to an X position within the source fiber, not the detector fiber.

Figure 5:
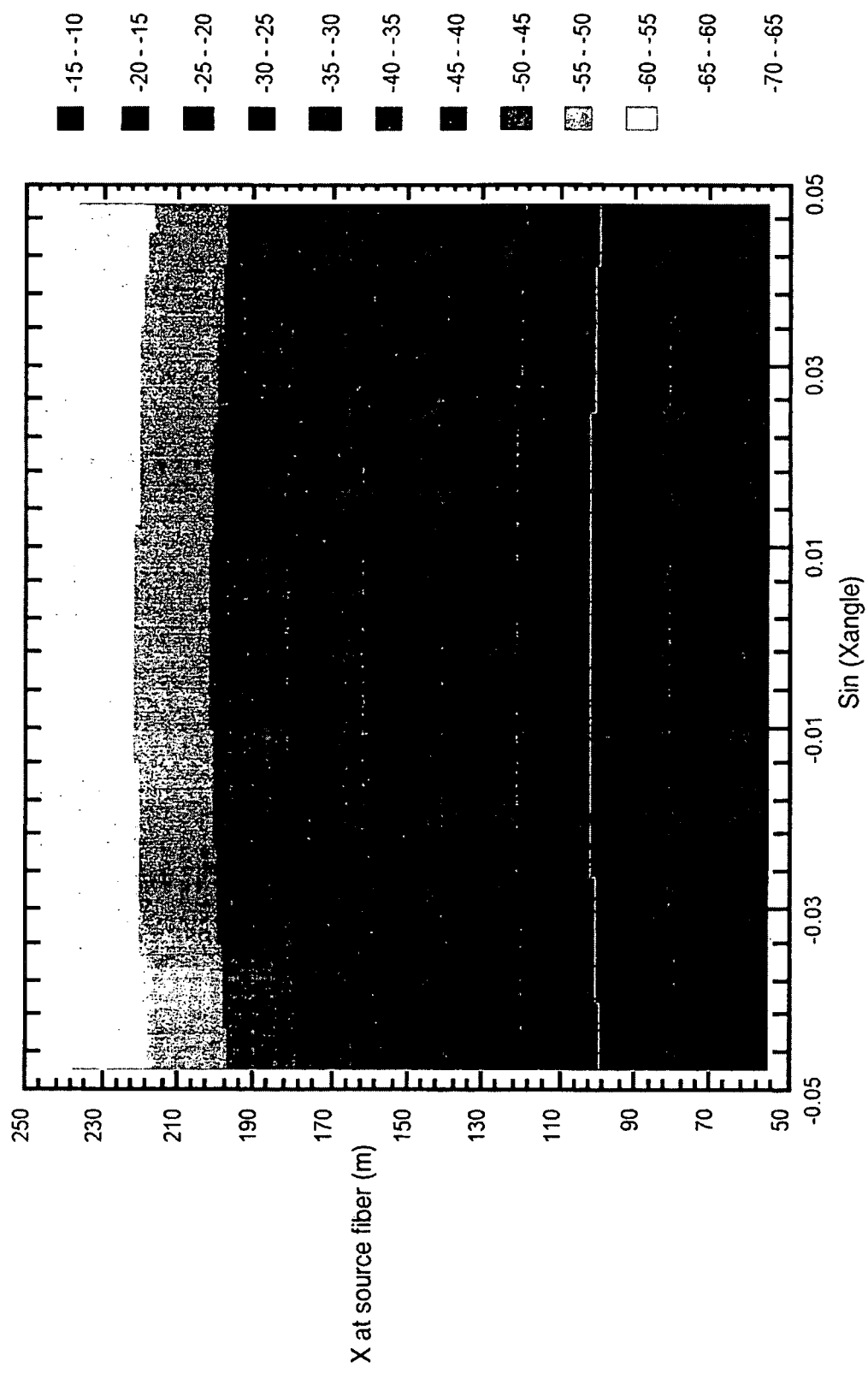

FIG. 5 is a continuation of the same simulation as is shown in FIG. 4, except the X position on the sample 20 is displayed versus X position of ray from source fiber 13a and sine of the starting ray angle. The span of X on the sample 20 ranges from −0.0125 to −0.064 mm, which is almost exactly a factor of 4 smaller (except sign reversed) than the edges of the source fiber core which are located at 0.05 and 0.25 mm. Thus, when the focus of the second off-axis paraboloid mirror 17 is coincident with the sample 20, the efficiency is essentially nil.

Figure 6:
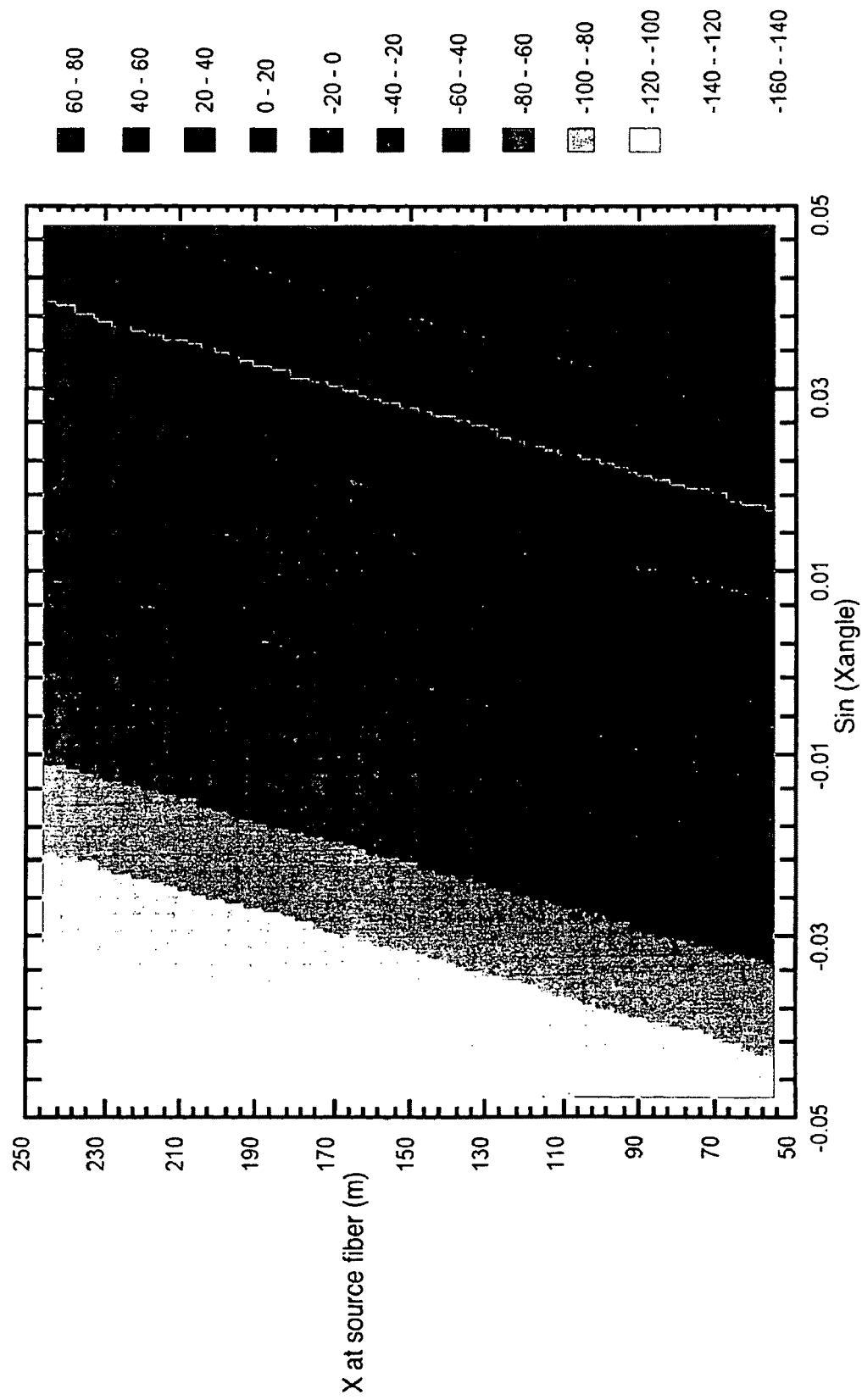

Next, a similar evaluation is performed, except z1 is set to 0.5 mm. FIG. 6 is a simulation of the final X position versus X position of a ray from the source fiber 13a and sine of the starting ray angle with z1 set to 0.5 mm. The final X position now spans a larger range, −0.733 to 1 mm; however, now some rays enter the detector fiber 13b.

Figure 7:
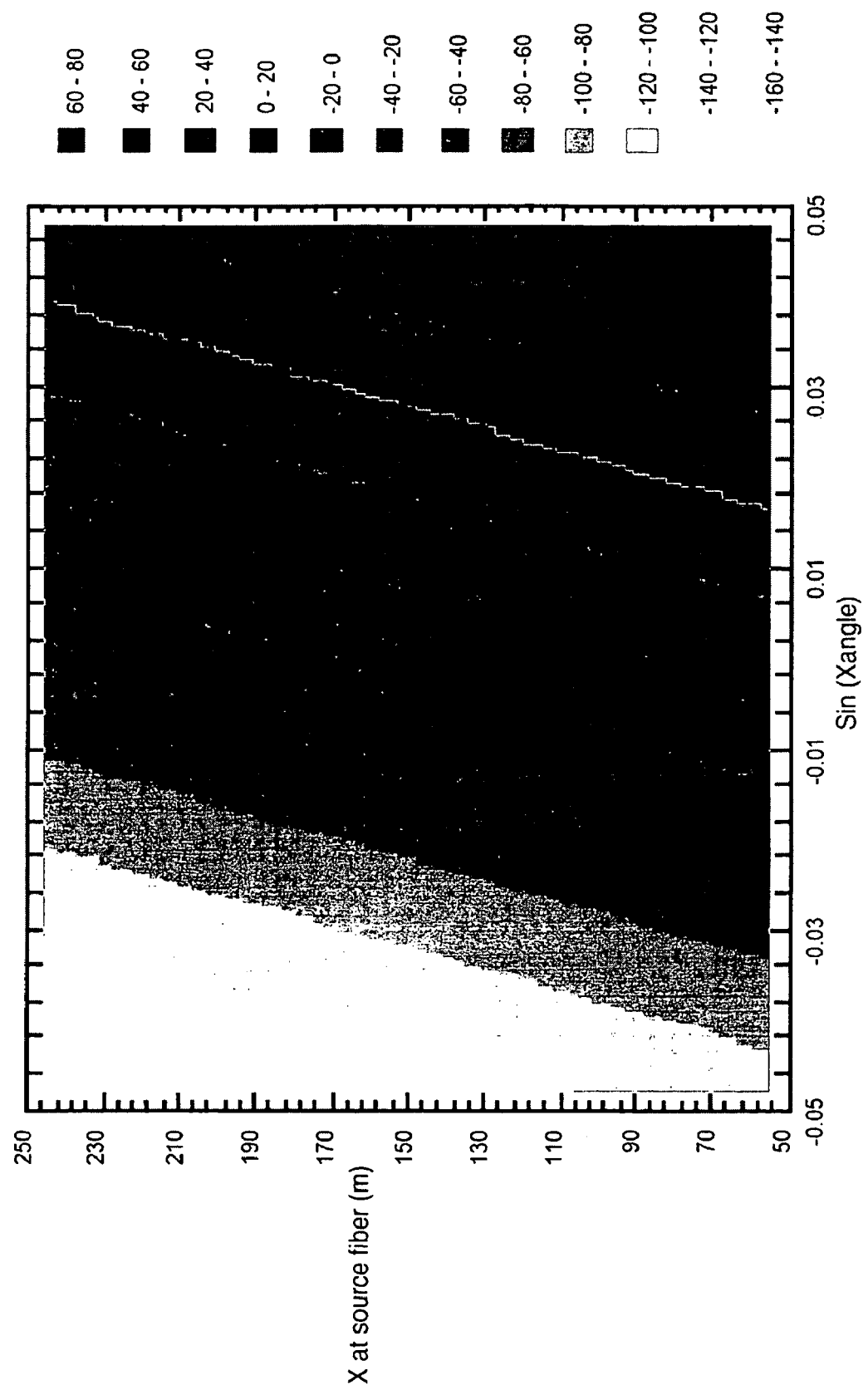

FIG. 7 is a simulation of the X position on the sample 20 versus X position of ray from source fiber and sine of the starting ray angle with z1 set to 0.5 mm. As can be observed on the above mentioned simulation graphs, although the illuminated region on the sample 20 is quite large compared to desired measurement spot size, rays that reach the detector only emanate from a region on the sample 20 smaller than desired spot size. A simulation of the relative percent efficiency versus the distance that the focus of the second paraboloid mirror is below the surface of the sample is shown in FIG. 8. As can be seen in the graph, the collection efficiency is quite sensitive to the distance that the focus of the second paraboloid mirror is below the surface of the sample. This sensitivity is quite useful in that it can be used to perform an auto focus operation. As already mentioned, the preferred embodiment of the invention combines a near-normal incidence ellipsometer in conjunction with a grazing angle ellipsometer. Upon initial set-up of the instrument the system is aligned so that the two measurement spots from the normal incidence ellipsometer and the grazing angle ellipsometer are coincident on the sample on a set-up sample and, the z height is set so that maximum reflection intensity is achieved. If however, a different sample is subsequently placed on the instrument that has a different thickness from the original set-up sample, then the spots are no longer necessarily coincident. If however, the sample is moved up and down iteratively to a find the position where the reflection intensity is at a maximum and then positioned such, then the two spots are coincident.

To view the position of the measurement beam on the sample 20, a video camera system 22-24 is employed as shown in FIG. 2. The signal from this camera system 22-24 may also be used by the pattern recognition system 26, so that the system 10 can automatically determine the current measurement position and direct the XY table to move accordingly to the desired measurement location on the sample 20.

The video camera system 22-24 and pattern recognition system 26 can be implemented in various ways. Referring again to FIG. 2, in a reduced to practice embodiment of the present invention, a fused silica beamsplitter 18 is disposed between the second off-axis paraboloid 17 and the sample 20. The illumination is supplied by the video camera system 22-24 and is shuttered off during measurement of the sample 20. In another embodiment of the invention, the video camera system 22-24 views the measurement area at an inclined angle as close to the sample normal as possible.

The optical design of the fiber-optic cable assembly 13 with the source fiber 13a and detector fiber 13b in close proximity in conjunction with the two-off-axis paraboloid mirrors 15, 17 is unique and novel in the art. The present invention solves several problems and has many advantages over the prior art. For example, the present invention has achromatic focusing with a small numerical aperture and no central obscuration of the aperture. The present invention provides for a single polarizer system 10 having essentially no collected back reflection from the polarizer 17. The present invention provides for a large working distance between the sample and the second paraboloid, thus allowing for placement of other optics components of the grazing angle ellipsometer that be necessity must be located in very close proximity to the sample.

Figure 3A:
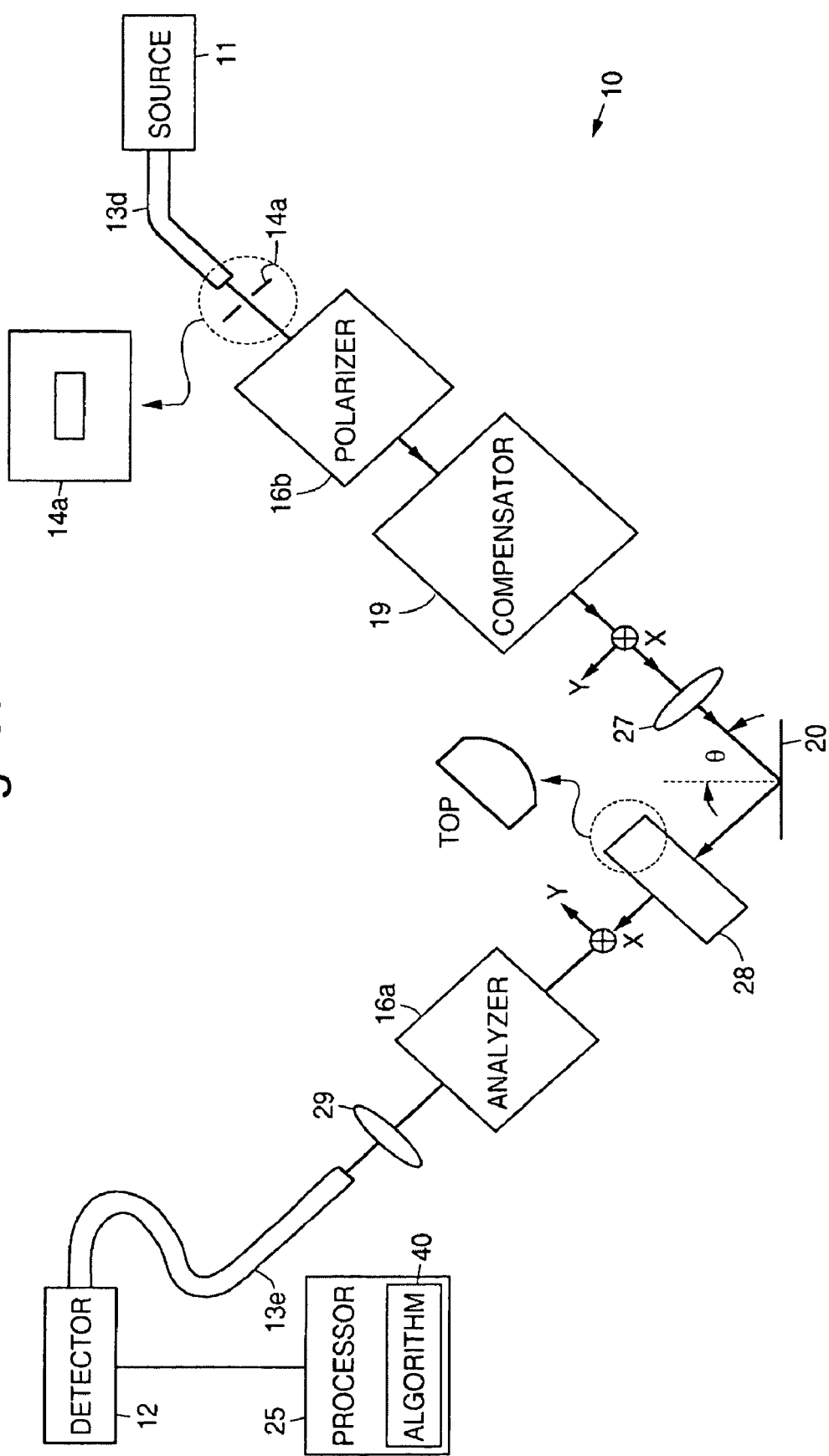
FIG. 3 illustrates an exemplary embodiment of a high angle of incidence metrology system in accordance with the principles of the present invention.
Figure 3C:
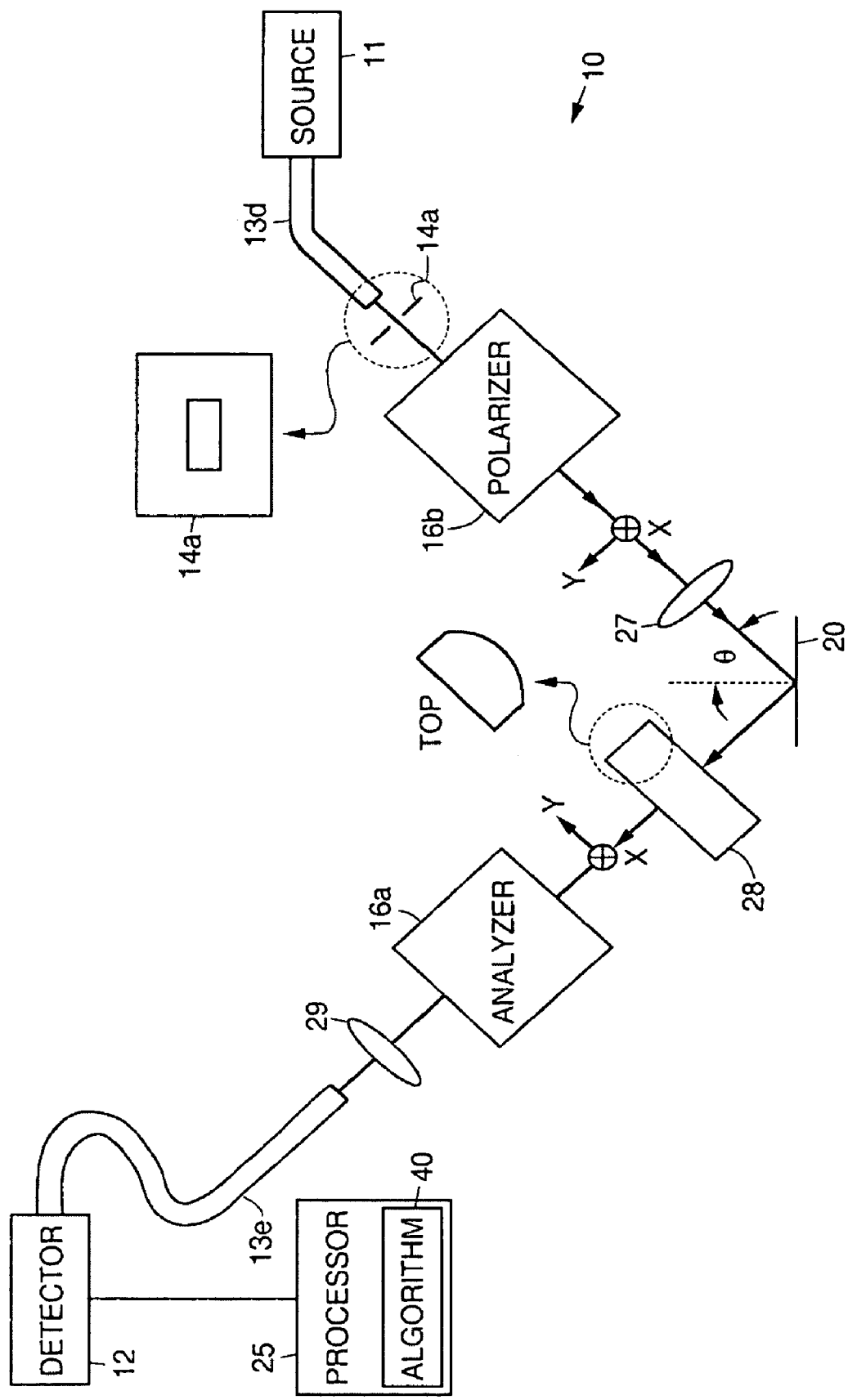

Referring to FIGS. 3a-3c, a variety of high angle of incidence spectroscopic ellipsometer-reflectometer systems 10 are described. FIGS. 3a-3c illustrates a grazing angle ellipsometer 10. In all embodiments of the grazing angle ellipsometer 10 a cylindrical lens 28 is employed between a sample 20 and an analyzer 16. The orientation of the cylindrical lens 28 is fixed it does not rotate. The grazing angle ellipsometer 10 may have three different configurations, namely, (a) a rotating compensator 19, with an analyzer 16 and polarizer 16 that are fixed during measurement, (b) a rotating polarizer 16 and a fixed analyzer 16 with the compensator 19 omitted, or (3) a rotating analyzer 16 and a fixed polarizer 16, with the compensator 19 omitted.

FIG. 3a shows a high angle of incidence system 10 that comprises a broadband source subsystem 11 and a detector subsystem 12. A source fiber-optic cable 13d couples the broadband source subsystem 11 to an input aperture of the ellipsometer-reflectometer system 10. A rectangular input field stop aperture 14a is disposed adjacent an output end of the source fiber-optic cable 13d. The aperture 14a is imaged by an objective 27 to approximately a square-shaped spot on a sample 20 to be measured. The objective 27 preferably comprises a single fused silica piano-convex lens 27.

A fixed polarizer 16b is disposed on the input side of the sample 20, a fixed analyzer 16a disposed on the output side of the sample 20, and a rotatable compensator 19 disposed between the fixed polarizer 16b and the sample 20. The rotatable compensator 19 rotates about an optical axis of the system, 10. A collection lens 29 is disposed between the analyzer 16a and a detector fiber optic cable 13e that couples electromagnetic radiation to the detector subsystem 12.

FIG. 3b shows a system 10 which is substantially similar to the system 10 shown in FIG. 3a, with slight modifications. In the system 10 shown in FIG. 3b, a fixed polarizer 16b is disposed on the input side of a sample 20 to be measured, a fixed analyzer 16a is disposed on the output side of the sample, and a rotatable compensator 19 disposed between the sample 20 and the fixed analyzer 16a. The rotatable compensator 19 rotates about an optical axis of the system 10.

FIG. 3c shows systems 10 that modify the systems 10 shown in FIGS. 3a and 3b. In the system 10 shown in FIG. 3c, a polarizer 16b is disposed on the input side of a sample 20, and an analyzer 16a is disposed on the output side of the sample 20. In one embodiment, the polarizer 16b is fixed and the analyzer 16a rotates about the optical axis of the system 10. In another embodiment, the analyzer 16a is fixed and the polarizer 16b rotates about the optical axis of the system 10. In another embodiment, the analyzer 16a and the polarizer 16b are fixed and a plano-convex cylindrical lens 28 is disposed between the sample 20 and the fixed analyzer 16a.

Additional details and operation of the systems 10 illustrated with regard to FIGS. 3a-3c will now be discussed.

For the purposes of further discussion, the x axis and y axis of the system 10 are defined as follows. A ray that travels along the optical axis is reflected by the sample 20 such that the optical axis changes direction after reflection from the sample 20. The x axis is orthogonal to a plane that contains both the incident and reflected rays and is also orthogonal to the optical axis. The y axis lies in the plane that contains both the incident and reflected rays and is also orthogonal to the optical axis.

In a preferred embodiment of the present invention, the rectangular aperture 14a is imaged by the focusing objective 27 onto the sample 20. The focusing objective 27 employed in a reduced to practice embodiment of the present invention is made of UV grade fused silica having a left surface radius of infinity, a right surface radius of 4.12 mm±0.08 mm, a surface quality of 40-20, a clear aperture of 90% of the central diameter, and a centration of 3 arc minutes.

A preferred shape of the rectangular aperture 14a illuminates a square region on the sample 20. The cylindrical lens 28 and collection lens 29 work together to collect rays from the sample 20 and image the square region on the sample 20 to a rectangular region on the plane of the detector fiber 13e. The detector fiber 13e then receives rays from a small section of the rectangular image.

A piano-convex cylindrical lens 28 focuses electromagnetic radiation in only one dimension. The piano-convex cylindrical lens 28 used in the present invention acts to collimate the electromagnetic radiation in only one dimension. In the other dimension, the cylindrical lens 28 has no optical power, and the rays continue to diverge. The net effect is that the cone angle collected in the dimension with no optical power is much smaller than the cone angle collected in the dimension with optical power. The cylindrical lens 28 essentially allows the system 10 to collect a large range of angles with respect to the x axis, and a small range of angles with respect to the y axis. Since the angle of incidence at the sample is primarily related to the angle with respect to the y axis, the range of angle of incidence at the sample is limited, however good efficiency is still maintained.

The optical design of the present systems 10 produces a small spot measurement, with a small range of angle of incidence on the sample 20, and yet has good efficiency, which is novel and unique.

Electromagnetic radiation from the source subsystem 11 is focused by optical elements within the source subsystem 11 onto the center of a fiber-optic output connector of the source subsystem 11. Both the source subsystem 11 and source fiber-optic cable assembly have mating SMA connectors.

The fiber-optic cable assembly 13d incorporates a single fiber preferably made of fused silica which transmits UV electromagnetic radiation. A preferred core diameter is 600 microns. This is the diameter used in a reduced to practice embodiment of the present invention.

Electromagnetic radiation travels along the source fiber 13d until it reaches the end of the fiber, at which point it emanates from the end in a diverging cone. The electromagnetic radiation next passes through a rectangular aperture plate 14a which is placed in very close proximity to the end of the source fiber 13d.

In a preferred embodiment, the rectangular aperture 14a has a rectangular opening of 600 microns along the x axis and 200 microns along the y axis. This aperture 14a is imaged by the focusing objective 27 onto the sample 20. For maximum efficiency, the desired target image shape of the aperture shape on the sample 20 is square.

The sample plane intersects the beam at an angle equal to the angle of incidence of the ellipsometer 10. The cross section of the beam on the sample 20 along the projection of the y axis on the sample is increased by a factor equal to the tangent of the angle of incidence. For an angle of 70 degrees, this factor is approximately 2.75. For this reason, the aperture opening along the y axis is made a factor 3 times smaller than aperture opening along the x axis. The aperture opening along the x axis is chosen to accept the electromagnetic radiation from the full diameter of the source fiber 13d, thus the 600 micron opening along the x direction. This produces a substantially square image of the aperture on the sample 20.

A focusing objective 27 is employed to image the rectangular aperture 14a onto the sample 20. The effective focal length is chosen so that there is reasonable clearance between the sample 20 and the objective 27, the desired demagnification is achieved, and the distance between the rectangular aperture 14a is not too long. The demagnification factor is approximately given by the ratio of the distance between the rectangular aperture 14a and the objective 27 and the effective focal length of the objective 27. In a reduced to practice embodiment of the present invention, a single fused silica piano-convex lens 27 is employed as the focusing objective 27. This plano-convex lens 27 has a diameter of 3 mm and an effective focal length of 9 mm. The distance between the rectangular aperture 14a and the sample 20 is 150 mm. This produces a measurement region smaller than 50 by 50 microns on the sample 20.

Typically in the prior art, to collect the reflected rays, an objective identical to the focusing objective 27 is placed after the sample. Although this design is very efficient, the range of angles of incidence on the sample is quite large, and in practice this makes measurement of thick films almost impossible and also greatly limits the capability of the instrument to accurately measure index of refraction and thickness of thin films.

In the present invention, in contrast to the prior art, the fused silica plano-convex cylindrical lens 28 is placed immediately after the sample 20. In a reduced to practice embodiment of the present invention, the effective focal length of the cylindrical lens 28 is 10 mm. In a preferred embodiment, the convex side faces the sample 20. The cylindrical lens 28 only has optical power along the x axis and no optical power along the y axis. The dimensions of the cylindrical lens 28 in the reduced to practice embodiment are 5 mm (along the y axis) by 9 mm (along the x axis).

Immediately before the detector fiber 13e, an optical element 29 with equal optical power along both the x and y axes is employed. For the purposes of further discussion, this is referred to as the detector fiber lens 29 (collection lens 29). In a reduced to practice embodiment of the present invention, a fused silica plano-convex lens 29 is employed. In the reduced to practice embodiment, the effective focal length of the plano-convex lens 29 is 10 mm. In the reduced to practice embodiment the piano side of the plano-convex lens 29 is closest to the detector fiber 13e. The diameter of the piano-convex lens 29 is 6 mm. The distance between the sample 20 and the plano-convex lens 29 is 150 mm.

Since the cylindrical lens 28 has no optical power along the y axis, the diameter of the detector fiber lens 29 is that of the effective aperture stop along the y axis. The y half-cone angle that can be collected by the detector fiber 13e is given approximately by the equation:

$$\text{Half-angle}(y) = \arctan(3/150) = 1.15 \text{ degrees}.$$

The range of angle of incidence on the sample 20 is approximately equal to angle of incidence of the ellipsometer+/−half-angle (y).

The angles along x are limited by the 3 mm diameter focusing objective 27 just prior to the sample 20.

$$\text{Half-angle}(x) = \arctan(1.5/9) = 9.46 \text{ degrees}$$

The fact that the system collects much higher angles with respect to the x axis than the y axis greatly increases efficiency, reduces measurement time, and still allows measurement of thick samples 20 since the range of angle of incidence on the sample 20 is small. This is illustrated in the simulated graphs of relative efficiency (number collected rays) with and without a cylindrical lens shown in FIG. 9.

The cylindrical and detector fiber lenses 28, 29 image the square region on the sample 20 to a narrow rectangle at the detector plane. At the detector plane, the rectangular image is much longer along the y axis than along the x axis. The detector fiber 13e samples a small section of the rectangular image.

In the reduced to practice embodiment of the present invention, a detector fiber 13e with a 600 micron core diameter is employed.

The CD algorithm will be discussed below.

Currently, there are several methods to determine critical dimension (CD) and trench depth. For example, see (1) Babar K. Minhas, Stephen A. Coulombe, S. Sohail H. Naqvi, and John R. McNeil (1 Aug. 1998 y Vol. 37, No. 22 page 5112 Applied Optics) "Ellipsometric scatterometry for the metrology of sub-0.1-mm-linewidth structures", (2) Petre C. Logofatu, Stephen A. Coulombe, Babar K. Minhas, and John R. McNeil (1108 J. Opt. Soc. Am. A/Vol. 16, No. 5/May 1999) "Identity of the cross-reflection coefficients for symmetric surface-relief gratings", and (3) Charles W. Haggans and Lifeng Li Raymond K. Kostuk (2217 Vol. 10 No 10/October 1993 J. Opt. Scoc. Am. A) "Effective-medium theory of zeroth-order lamellar gratings in conical mountings".

To replicate actual semiconductor processes, the CD structure is constructed of many layers under the actual grating (repeated CD lines). In practice, one is mainly interested in the line widths, depth, and profiles of the top layer. Unfortunately, all conventional methods are extremely sensitive to the optical properties of not only the measured grating structure but also to the layers underneath. Any variation in the thickness or optical properties of these layers tends to produce large errors in the measured CD.

The present invention overcomes these difficulties by introducing the concept of relative shift (ratio) of the power spectral density of differential polarimetry to decouple the measurement of the grating (CD) structure from the underneath layers (structure). The present invention is particularly applicable to thick films>λ/4.

Figure 14:
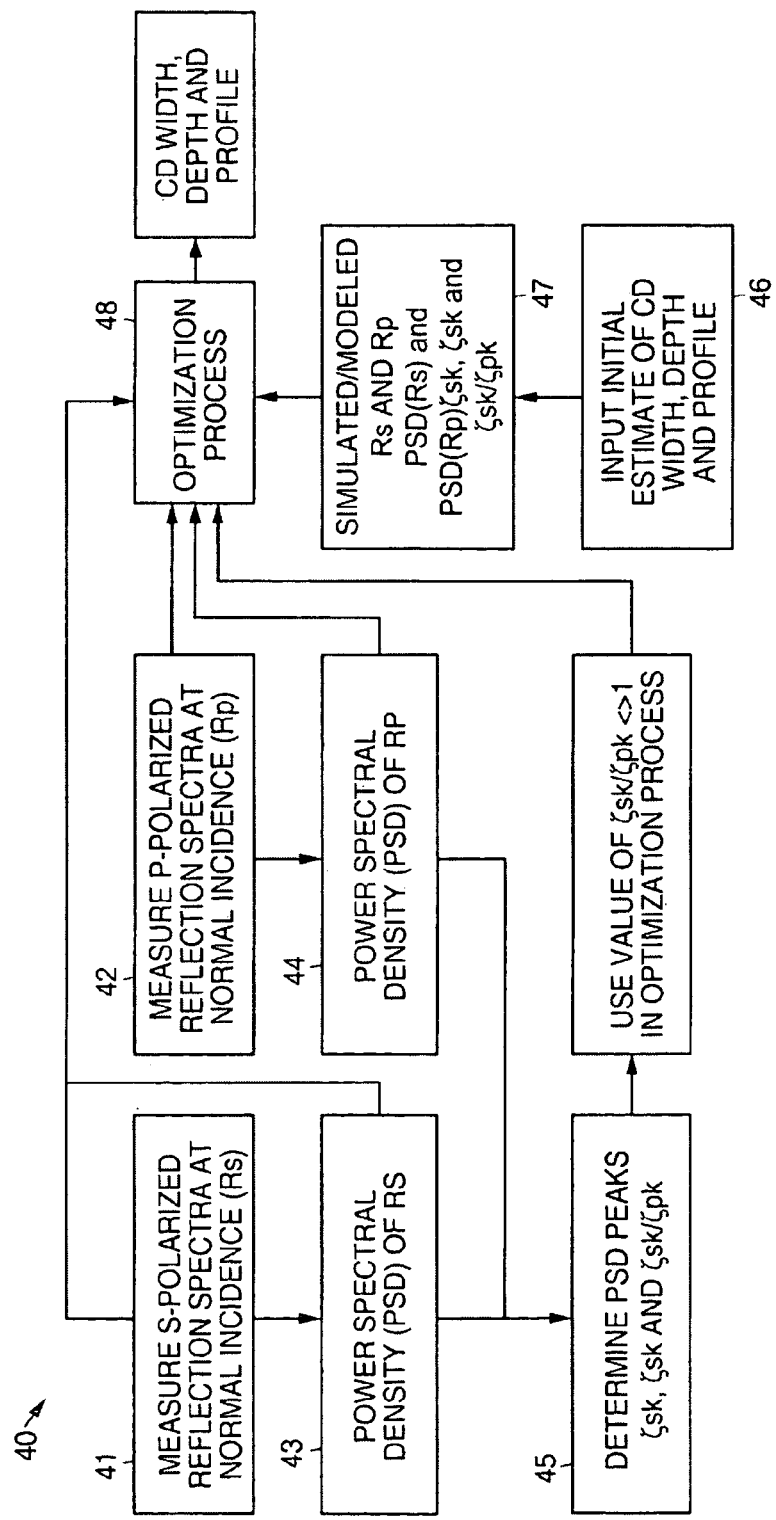
FIG. 14 is a flow diagram illustrating an exemplary method or algorithm implemented in accordance with the principles of the present invention.

FIG. 14 is a flow diagrams illustrating an exemplary algorithm 40 implemented in accordance with the principles of the present invention. The algorithm 40 runs on the processor 25. The algorithm 40 implements a measurement and calculation method 40 in accordance with the principles of the present invention.

The first step is to measure the 41 s-polarized reflection spectrum ($R_s$) at substantially normal incidence. The next step is to determine 42 or compute 42 the power spectral density (PSD) of $R_s$. The next step is to measure the 43 p-polarized reflection spectrum ($R_p$) at substantially normal incidence. The next step is to determine 44 or compute 44 the power spectral density (PSD) of $R_p$. The PSD peaks $\zeta_{sk}$, $\zeta_{sk}$ and $\zeta_{sk}/\zeta_{pk}$ are determined 45 or computed 45. The value of $\zeta_{sk}/\zeta_{pk}$<>1 is used in an optimization process 48.

The next step is to input 46 an initial estimate of critical dimension (CD) width, depth, and profile to a simulation/model 47. The simulation/model 47 computes estimates of $R_s$ and $R_p$, PSD ($R_s$) and PSD ($R_p$), and $\zeta_{sk}$, $\zeta_{sk}$ and $\zeta_{sk}/\zeta_{pk}$ based upon the model. The optimization process 48 uses the values generated by the simulation/model 47 along with the corresponding measured and computed values to generate and output actual CD width, depth, and profile for the sample 20 under measurement.

More particularly, the present invention measures the critical dimension (CD) structure of a multi-layer thin film structure 32 disposed on a substrate 31 with minimal effect from the layers 32 underneath a grating structure 31, such as is shown in FIG. 10. This is achieved by measuring normal incident reflectance and/or ellipsometric parameters at normal incidence over a wide spectral range, using a spectrophotometer, for example, and then applying the following methodology 40 to determine the CD of the top layer.

Measure 41, 42 the normal incident reflection spectra at two different polarizations ($R_s$ and $R_p$). Since the multi-layer thin film structure 32 and the substrate 31 in the CD structure are non-birefringent the difference in the reflectance between the two polarizations is only a function of the CD grating structure 31. To amplify the difference between the two polarizations:

Calculate 43, 44 the power spectral density of the measured reflection spectra for both polarizations as a function of frequency.

Determine 45 the statistically significant peaks of the power spectral density (PSD). For a single layer one needs to consider only the most significant peak (maximum peak). The parameters $\xi_s^j$ and $\xi_p^j$ are defined as the position of peak j of PSD of the polarization state s and p.

This step determines 45 $\xi_s^j$, $\xi_p^j$ and $\xi_s^j/\xi_p^j$.

The peaks that have a value of $\xi_s^j/\xi_p^j=1$ are due to the multilayer structure underneath the grating. The grating layer (cd) acts as a birefringent layer and has a value different than one ($\xi_s^j/\xi_p^j<>1$), this value is defined as $R_\xi$. To first order, $R_\xi$ is independent of the thickness the layers and only a function the CD spacing and shape. In the limit where the CD spacing is <<λ, an effective medium approximation (EMA) can be used in the optimization process 48 to easily extract the CD spacing and profile.

EXAMPLE

Figure 12:
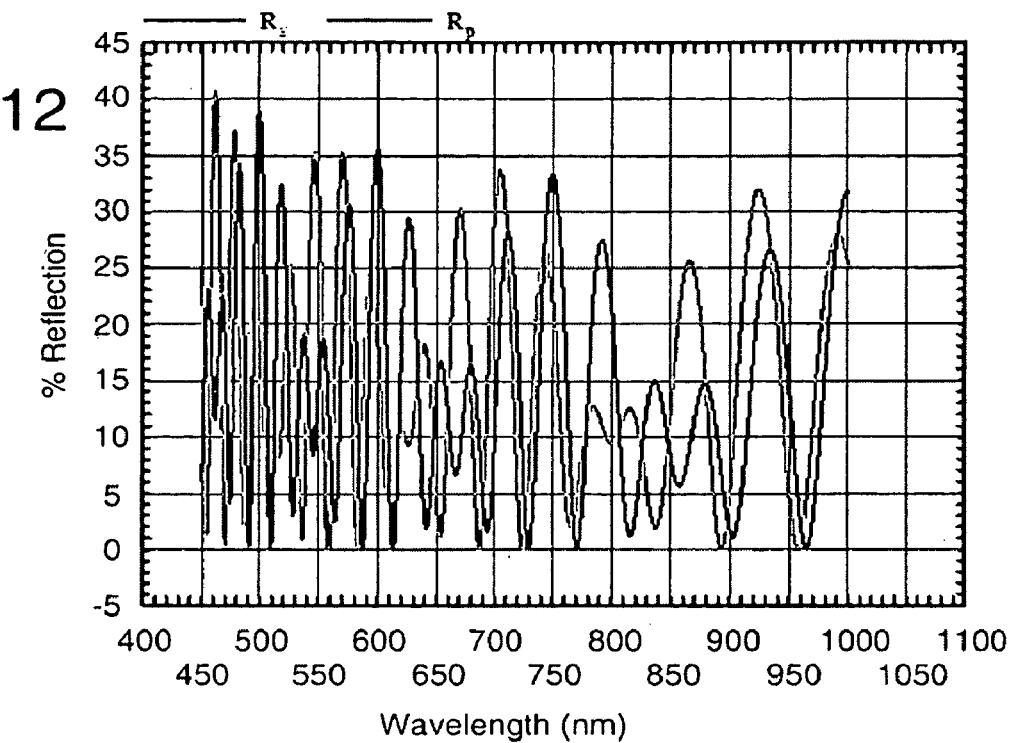
FIG. 12 is a graph showing percent reflection versus wavelength for an exemplary CD structure (stack)

To illustrate the significance of the present method 40 consider a simple example of a two-layer transparent (k=0) stack 30 shown in FIG. 11, where a layer 32 next to a silicon substrate 31 has a constant index of refraction (no dispersion) of $n_1$=2 and thickness $T_1$=2_m, and the top layer 33 has an index $n_2$=1.5 and a thickness $T_2$=1_m. A graph showing percent reflection versus wavelength for the stack 30 is shown in FIG. 12. If one performs a PSD (R); power spectral density analysis of the polarized reflection magnitude (FIG. 9) as a function of frequency, one finds that there are three PSD (R) peaks (shown in FIG. 13)

Figure 13:
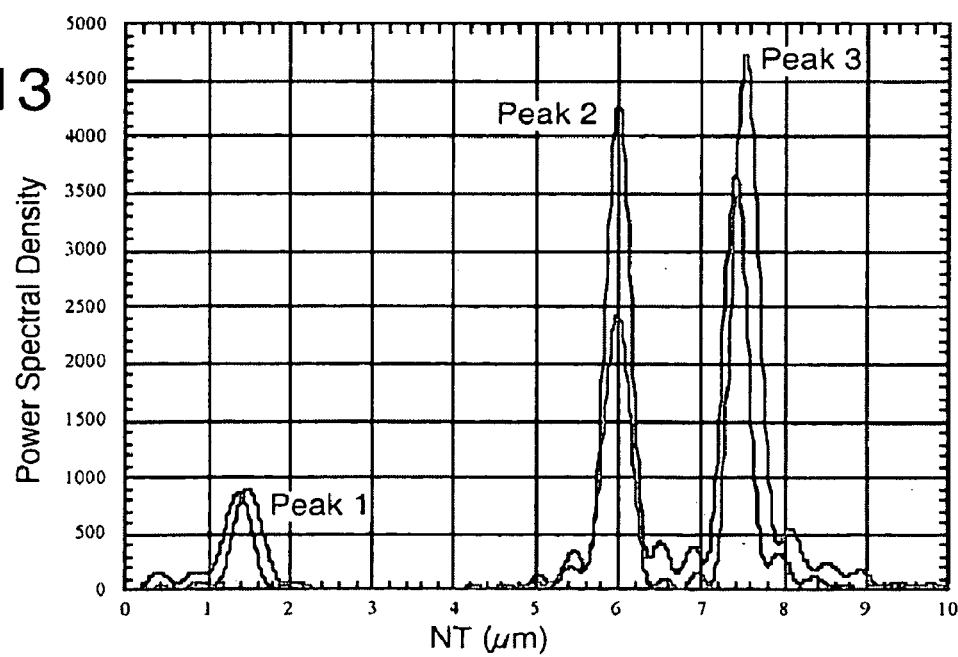
FIG. 13 is a graph showing power spectral density versus optical thickness (index of refraction*thickness, NT)

As is shown in FIG. 13, the first peak represents the top grating layer 33, the second peak represent the bottom layer 32 next to the substrate 31, while the third peak represent the total stack 30. There is no shift in the PSD peak position of the bottom layer 32 (Rξ of the second peak=1). To first order in (_/λ), where _ is the grating period, one can define two indices of refraction for the grating layer 33 (see Charles W. Haggans and Lifeng Li Raymond K. Kostuk (2217 Vol. 10 No 10/October 1993 J. Opt. Scoc. Am. A) "Effective-medium theory of zeroth-order lamellar gratings in conical mountings").

$$n_o^2 = n_2^2(1-D) + D \qquad \text{Eq. 1}$$

-continued $$n_e^2 = \frac{n_2^2}{n_2^2 D + 1 - D} \qquad \text{Eq. 2}$$

where D is defined as (D=a/_), where a is the spacing between the $n_2$ lines as shown in FIG. 11.

$$\zeta_{1s} = n_o T_2 \qquad \text{Eq. 3}$$

$$\zeta_{1p} = n_e T_2 \qquad \text{Eq. 4}$$

The ratio of the $\zeta_{1s}$ to $\zeta_{1p}$ is given by $$R\zeta_1 = \frac{\zeta_{1s}}{\zeta_{1p}} = \frac{n_o}{n_e} \qquad \text{Eq. 5}$$

Note that the CD parameter (D) can be independently determined from $R\zeta_1$ with no influence from the bottom layer.

$$D = f(R\zeta_1, n_2) \qquad \text{Eq. 6}$$

The thickness (depth) of the CD structure ($T_2$) can be simultaneously determined from Eq. 3.

The present invention combines the normal incidence polarized reflection, normal incidence ellipsometry, and near grazing angle reflectometry and ellipsometry; these data can be combined to not only resolve the line width (D) but also the profile and CD structure and the optical properties of the multilayer stack.

Figure 15:
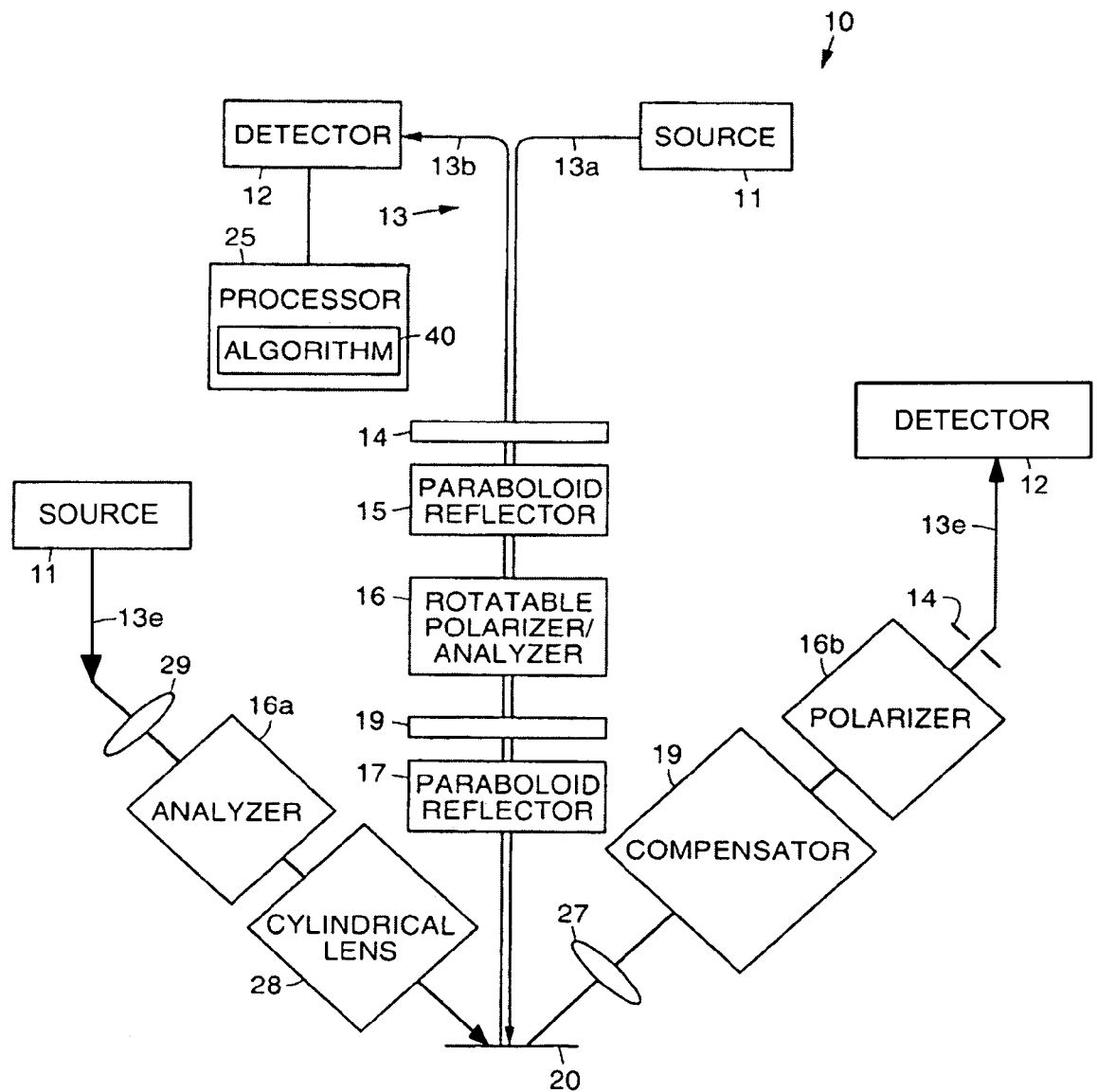
FIG. 15 shows a preferred embodiment of the present invention.

Although the above-preferred embodiments have been described with specificity, persons skilled in this all will recognize that many changes to the specific embodiments disclosed above could be made without departing from the spirit of the invention. For example, by reference to FIGS. 1 and 15, it should be recognized that the position of source 11 and detector 12 can be swapped so that it is possible to connect the detector fiber to the light source and connect the source fiber to the detector. The same measurement results are achieved with no change to software calibration or software operation. The direction of the light is swapped and, technically, the polarizer becomes the analyzer and the analyzer becomes the polarizer. Therefore, the attached claims and their legal equivalents should determine the scope of the invention.

We claim:

1. An apparatus for performing measurements of unpatterned and patterned thin films on semiconductor microelectronic wafers, comprising:
    a near-normal incidence metrology system comprising:
    a broadband electromagnetic radiation source;
    a detector system for outputting electrical signals corresponding to electromagnetic radiation detected thereby;
    focusing apparatus comprising first and second off-axis parabolic reflectors for focusing electromagnetic radiation derived from the source onto a sample under measurement;
    a rotatable polarizer disposed between the first and second off-axis parabolic reflectors and further comprising a rotatable compensator disposed between the rotatable polarizer and one of the parabolic reflectors, and
    an optical coupling apparatus that couples electromagnetic radiation from the electromagnetic radiation source to the focusing apparatus, and couples electromagnetic radiation reflected from the sample to the detector system.

2. The apparatus recited in claim 1 further comprising a video camera system optically coupled to view the sample, and a pattern recognition system coupled to the video camera for detecting thin film patterns on the sample.

3. The apparatus recited in claim 1 wherein the optical coupling apparatus comprises a fiber optic cable system comprising a source fiber and a detector fiber that respectively couple the source subsystem to the optical coupling apparatus, and couples the optical coupling apparatus to the detector subsystem.

4. The apparatus recited in claim 3 wherein the fiber optic cable system comprises source and detector fibers that are symmetrically disposed and are offset from a center of the axis of the cable system adjacent their respective output and input ends.

5. The apparatus recited in claim 1 further comprising a high angle of incidence metrology system comprising: a source fiber optic cable coupled to the source; a polarizer coupled between the source and the sample; a focusing objective coupled between an output end of the source fiber optic cable and the sample; a detector fiber optic cable coupled to the detector system; an analyzer coupled between an input end of the detector fiber optic cable and the sample; a detector lens coupled between the input end of the detector fiber optic cable and the analyzer; a plano-convex cylindrical lens coupled between the sample and the analyzer.

6. The apparatus recited in claim 5 further comprising a rectangular field stop aperture disposed adjacent an output end of the source fiber-optic cable.

7. The apparatus recited in claim 5 wherein the objective comprises a fused silica plano-convex lens.

8. The apparatus recited in claim 5 wherein the analyzer is rotatable.

9. The apparatus recited in claim 5 wherein the apparatus further comprises a rotatable compensator disposed between the source and the sample.

10. The apparatus recited in claim 5 and further comprising a rectangular field stop aperture disposed adjacent an output end of the source fiber-optic cable.

11. The apparatus recited in claim 5 wherein the cylindrical lens comprises a fused silica plano-convex lens.

12. The apparatus recited in claim 5 wherein the analyzer is rotatable.

13. The apparatus recited in claim 5 wherein the analyzer is fixed.

14. The apparatus recited in claim 5 wherein the analyzer is fixed and the apparatus further comprises a rotatable compensator disposed between the source and the sample.

15. An apparatus for performing measurements of unpatterned and patterned thin films on semiconductor microelectronic wafers, comprising:
    a near-normal incidence metrology system comprising:
    a broadband electromagnetic radiation source;
    a detector system for outputting electrical signals corresponding to electromagnetic radiation detected thereby;
    focusing apparatus comprising first and second off-axis parabolic reflectors for focusing electromagnetic radiation derived from the source onto a sample under measurement;
    a fixed polarizer disposed between the first and second off-axis parabolic reflectors and further comprising a rotatable compensator disposed between the fixed polarizer and one of the parabolic reflectors, and
    an optical coupling apparatus that couples electromagnetic radiation from the electromagnetic radiation source to the focusing apparatus, and couples electromagnetic radiation reflected from the sample to the detector system.

16. An apparatus for performing measurements of unpatterned and patterned thin films on semiconductor microelectronic wafers, comprising:
 a near-normal incidence metrology system comprising:
 a broadband electromagnetic radiation source;
 a detector system for outputting electrical signals corresponding to electromagnetic radiation detected thereby;
 focusing apparatus comprising first and second off-axis parabolic reflectors for focusing electromagnetic radiation derived from the source onto a sample under measurement;
 a fiber optic cable system comprising a source fiber and a detector fiber that respectively couple the source subsystem to the optical coupling apparatus, and couples the optical coupling apparatus to the detector subsystem wherein the fiber optic cable system comprises source and detector fibers that are symmetrically disposed and are offset from a center of the axis of the cable system adjacent their respective output and input ends, and
 an optical coupling apparatus that couples electromagnetic radiation from the electromagnetic radiation source to the focusing apparatus, and couples electromagnetic radiation reflected from the sample to the detector system.

* * * * *